United States Patent
Moss et al.

(10) Patent No.: US 6,982,929 B2
(45) Date of Patent: Jan. 3, 2006

(54) HEIGHT MEASUREMENT METHOD AND APPARATUS

(75) Inventors: Scot A. Moss, Duarte, CA (US); John W. Waguespack, Redondo Beach, CA (US); Warren J. Wilson, Fullerton, CA (US); Gary E. Krekemeyer, Newport Beach, CA (US)

(73) Assignee: Disney Enterprises, Inc., Burbank, CA (US)

(*) Notice: Subject to any disclaimer, the term of this patent is extended or adjusted under 35 U.S.C. 154(b) by 30 days.

(21) Appl. No.: 10/310,561

(22) Filed: Dec. 4, 2002

(65) Prior Publication Data

US 2003/0159300 A1 Aug. 28, 2003

Related U.S. Application Data

(60) Provisional application No. 60/336,842, filed on Dec. 4, 2001.

(51) Int. Cl.
*G01S 15/00* (2006.01)
(52) U.S. Cl. .................. 367/99; 181/124; 33/832; 33/512
(58) Field of Classification Search .......... 33/832, 33/833, 512, 515; 356/625, 630; 181/124; 367/99, 908; 705/13; 40/633, 665
See application file for complete search history.

(56) References Cited

U.S. PATENT DOCUMENTS

| | | | |
|---|---|---|---|
| 2,215,884 A * | 9/1940 | Runge | 33/512 |
| 3,184,969 A | 5/1965 | Bolton | |
| 3,795,396 A * | 3/1974 | Kropelnitski | 482/8 |
| 4,336,855 A | 6/1982 | Chen | |
| 4,412,384 A * | 11/1983 | Viets | 33/512 |
| 4,518,052 A | 5/1985 | Chen | |
| 4,539,754 A * | 9/1985 | Antony et al. | 33/515 |
| 4,923,024 A | 5/1990 | Torres et al. | |
| 5,255,301 A * | 10/1993 | Nakamura et al. | 377/6 |
| 5,305,390 A | 4/1994 | Guthrie et al. | |
| 5,364,133 A * | 11/1994 | Hofer et al. | 40/633 |

(Continued)

FOREIGN PATENT DOCUMENTS

JP 02239843 A * 9/1990

(Continued)

OTHER PUBLICATIONS

If you take your kids to ONE park, this is the place to go!, Aug. 26, 2000, p. 2.*

(Continued)

*Primary Examiner*—Christopher W. Fulton
*Assistant Examiner*—Amy R. Cohen
(74) *Attorney, Agent, or Firm*—Greenberg Traurig, LLP; Margo Maddux; Neer Gupta, Esq.

(57) ABSTRACT

The present invention provides for a system and method for measuring the height of a guest at a theme park, including employing an ultrasonic emitter and sensor to determine height. The park may have a plurality of different predetermined minimum height ranges or categories for certain rides and attractions, which must be met by a guest before the guest is allowed to participate. The results of the height measurement are provided on indicia and given to the guest to use at rides throughout the park. The device may be a wristband affixed to the guest, and displaying a color or symbol based on the height of the guest. The guest would be allowed to participate in an attraction provided the color code matches the minimum requirements of the attraction. This present invention may eliminate the need to check the height of the guest at each ride.

18 Claims, 10 Drawing Sheets

U.S. PATENT DOCUMENTS

| | | | |
|---|---|---|---|
| 5,379,028 A | | 1/1995 | Chung |
| 5,400,722 A | * | 3/1995 | Moses et al. .................. 109/2 |
| 5,566,327 A | * | 10/1996 | Sehr ........................ 707/104.1 |
| 5,813,132 A | | 9/1998 | Bodkin, Sr. |
| 5,877,997 A | | 3/1999 | Fell |
| 5,979,941 A | * | 11/1999 | Mosher et al. ................ 40/633 |
| 5,996,240 A | | 12/1999 | Casper |
| 6,055,756 A | * | 5/2000 | Aoki ........................... 40/633 |
| 6,119,096 A | * | 9/2000 | Mann et al. .................... 705/5 |
| 6,237,239 B1 | * | 5/2001 | Miyazaki ..................... 33/512 |
| 6,302,122 B1 | | 10/2001 | Howard et al. |
| 6,327,494 B1 | * | 12/2001 | Sakai ......................... 600/547 |
| 6,847,586 B1 | * | 1/2005 | Chen .......................... 367/99 |

FOREIGN PATENT DOCUMENTS

| | | | | |
|---|---|---|---|---|
| JP | 10111959 A | * | 4/1998 | |
| JP | 10211189 A | * | 8/1998 | |
| JP | 2000066610 A | | 8/1998 | |

OTHER PUBLICATIONS

Perfect for pre-schoolers; Nov. 28, 2000; p. 2.*

McGovern, Matthew A.; Is Your Playground Equipment Safe?; Jun., 2000; p. 1.*

Royal Caribbean International Implements New Youth Evacuation Plan; Oct. 2001, p. 1.*

Emmons, Natasha; Height-check System Debuts; Jan. 7, 2002; p. 1.*

What Some Will Do to Get In Free: Schemes, Shams & Scams of Sneaks; Feb. 20, 1995; p. 2.*

Disneyland Resort Introduces New Height-Measurement System as Part of Global Safety Program; Dec. 18, 2001; p. 1.*

Kite, Sarah; Wet and Wild Local Water Parks Sure to Cool You Down; Jul. 17, 2003; p. 3.*

Vacation 1999: Day Seven; 2000; p. 9.* http://ourworld.compuserve.com/homepages/tektektek/dl2000.htm; p. 8.*

Kings Dominion Unofficial Guide, pp. 1-13.*

General Attraction and Height Discussion document; Six Flags Over Georgia; playride.com.*

Dorney Park and Wildwater Kingdom document; dorneypark.com.*

Disney Themem Park Info-Height Requirements, Aug. 18, 2000.* www.mousetyme.com; May 25, 2002.*

* cited by examiner

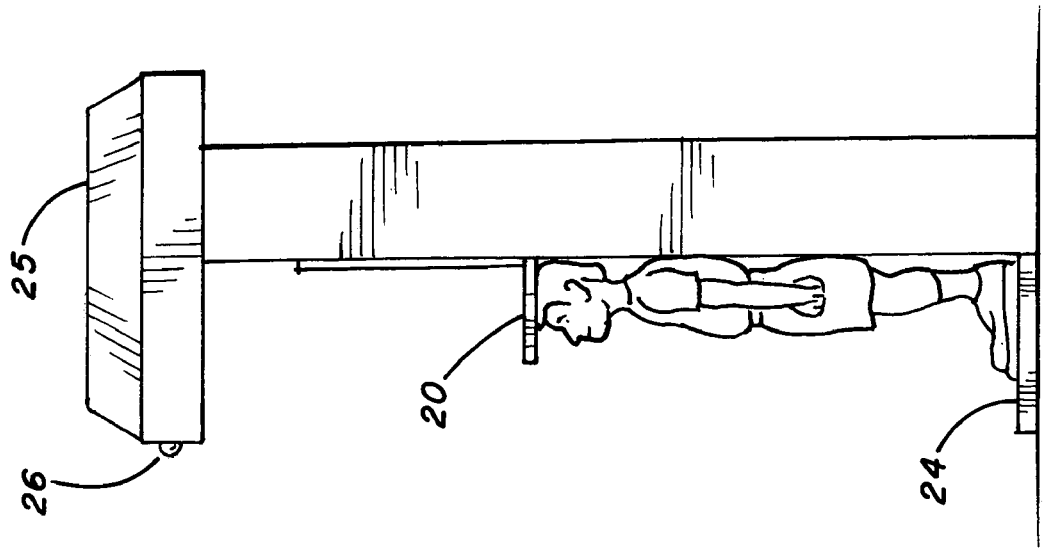
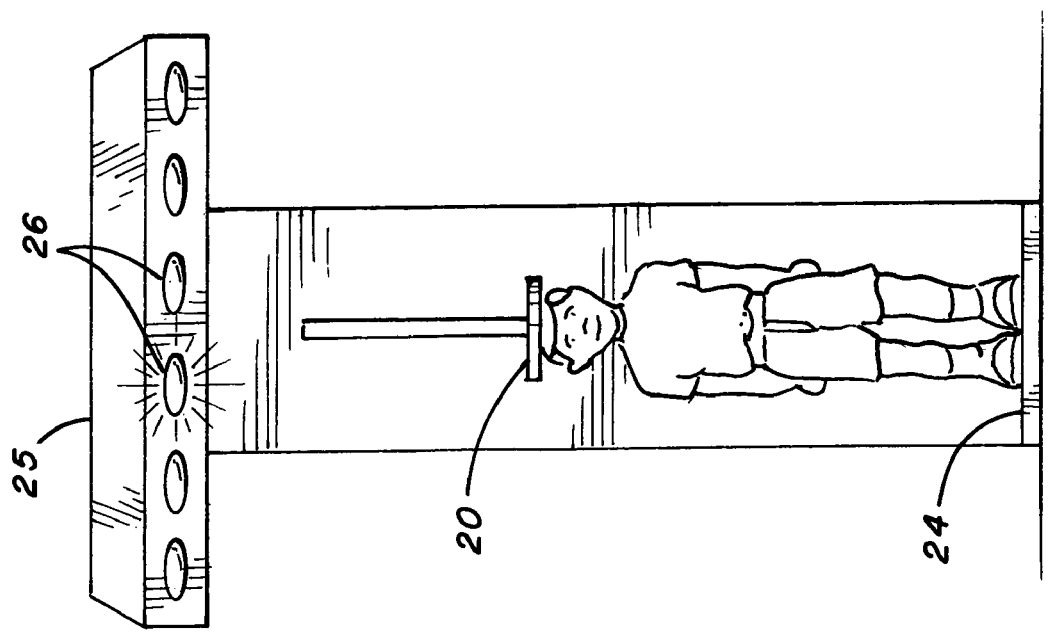

FIG. 5A
FIG. 5B
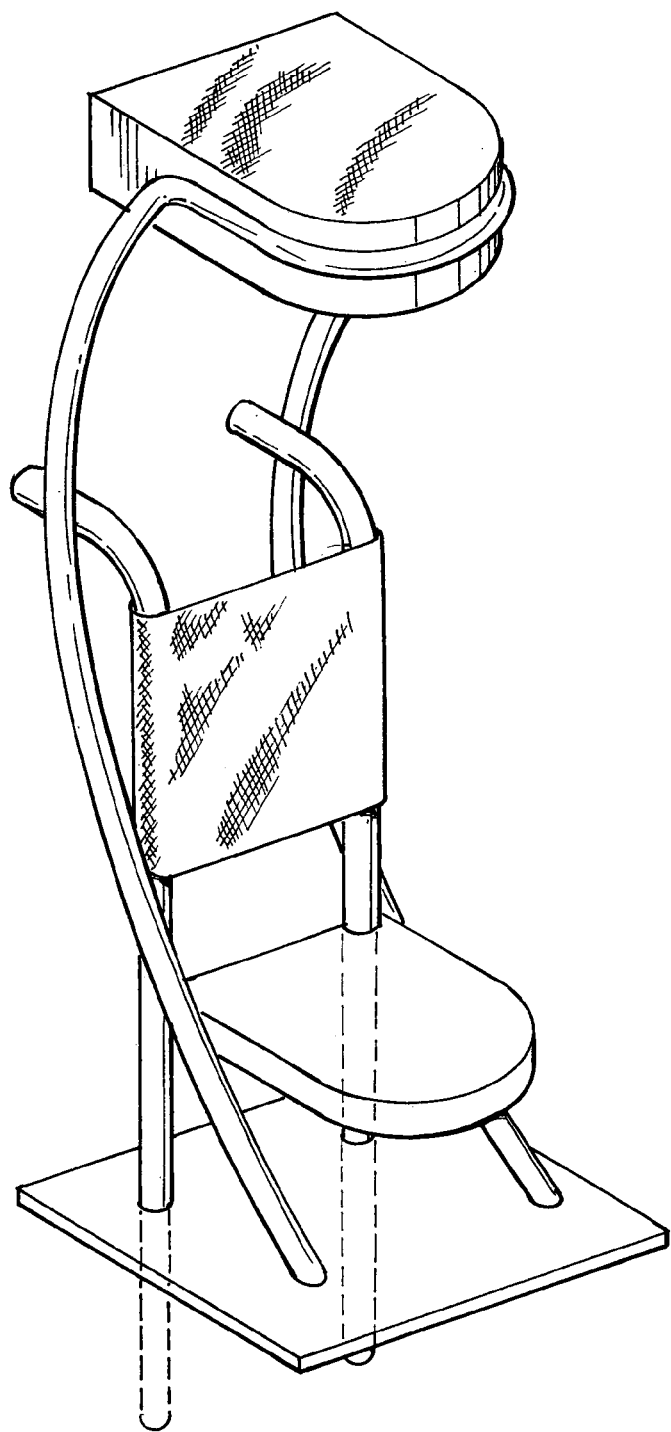
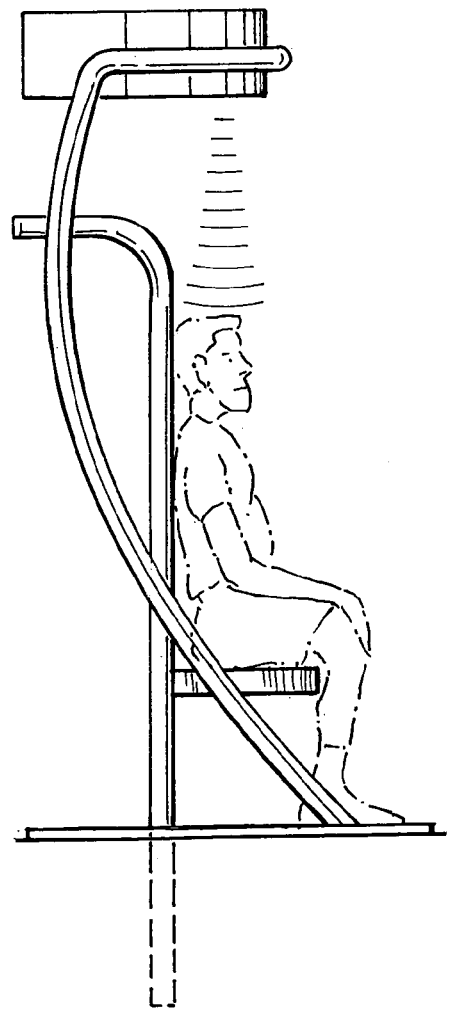

HEIGHT MEASUREMENT METHOD AND APPARATUS

RELATED APPLICATIONS

This application claims priority to U.S. Provisional Application Ser. No. 60/336,842 entitled "Height Check Apparatus and Method," filed on Dec. 4, 2001 which is incorporated herein by reference in its entirety.

BACKGROUND OF THE INVENTION

1. Field of the Invention

The present invention relates generally to systems and methods of measuring a person's height at a venue, such as an amusement park. The present invention relates more particularly to methods of managing entrance to a ride or attraction at a theme park according to height requirements.

2. General Background and State of the Art

In many resorts, such as theme parks, attractions and rides place limits on the acceptable heights of a patron or guest participating in the attraction or ride. Most often, this will be a limit on the minimum height of a guest, and may be chosen for safety reasons or to ensure that the guest will have an acceptable view of the surroundings in the attraction. Within one resort or park, a number of attractions may each have different height limits, and the measurement methods may vary from attraction to attraction. For example, a resort may have 16 attractions that require employees to measure guests manually for five different heights of 52 inches, 48 inches, 46 inches, 40 inches and 35 inches. A guest at such a resort typically will be measured at each attraction individually, before the guest is permitted to participate.

Presently, such resorts generally employ a manual height verification system to monitor the height requirements for various attractions, relying on the judgment of individual attraction operators in the use of various incompatible height markers or measurement systems unique to each attraction.

There is a need for a standardized height measuring apparatus and method that eliminates the need for multiple measurements of guests at various attractions, and increases measurement consistency.

INVENTION SUMMARY

It is therefore an object of the present invention to provide a convenient system and method of measuring the height of a guest at a theme park. The present invention accomplishes these and other objects by providing guests and employees with a single consistent height measurement that enhances their experiences visiting and/or working at the park. The invention provides a standardized and mechanized measuring system that ensures an objective and consistent measurement approach for the guest and employee throughout the resort, eliminating the need for multiple measurements of guests at each ride location and the frustration of dealing with the inconsistencies found in existing manual systems.

The apparatus and method of the present invention further provides a coding system including indicia associated with the height of a guest as measured by the apparatus of the present invention. For example, the indicia may include different colored wristbands affixed to the guest, each color representing a specific height or height range. The attractions are individually color-coded corresponding to the height limitations at each attraction. Each attraction can be designated as accepting guests wearing certain colors of wristbands, which represent heights acceptable for entering the attraction. Notices may be posted throughout the park and/or in park guide maps and handouts indicating the requirements for each attraction by utilizing the indicia, such as the color-coding.

The height measurement apparatus of the present invention uses sound waves to accurately measure a guest's height. Ultrasonic waves can be used to effectively measure distances without contact. Distance measurement using ultrasonic waves can be accurate to 0.05% of range, which equates to ±0.002 in. at a distance of 4 inches. An ultrasonic transducer/sensor is mounted in a stationary position above a person's head. The person stands or sits underneath the sensor. The transducer sends an ultrasonic pulse. The pulse is reflected when it reaches the top of the person's head, and returns to the sensor. The amount of time for this travel is measured, and can be translated into distance.

In a preferred embodiment of the present invention, a paddle is placed to rest on top of the person's head in order to more accurately reflect the signal. The paddle may preferably have a level indicator to help the operator keep the paddle level. A tilted paddle can lead to an inaccurate measurement. The paddle may also preferably have a button in the handle to allow the operator to signal taking a height measurement.

A programmable logic controller is coupled with the ultrasonic transducer to measure guest height. The height measurement apparatus also comprises a display to report the results of the measurement. This display may or may not be available for viewing by the guest. The apparatus may also include reporting elements such as lights or sound. A power saving feature turns off the ultrasonic sensor when the height measurement apparatus is not in use. The height measurement apparatus is powered by either AC or DC power.

The height measurement apparatus sits idle until a button is pressed to initiate taking a measurement. When the button is pressed, the programmable logic controller (PLC) energizes the ultrasonic transducer. In a preferred embodiment of the present invention, the ultrasonic transducer takes 4 readings. These four readings are averaged and the result is offset by calibration values obtained when the unit is zeroed. This value is proportional to the guest's height.

The height measurement apparatus may measure a guest's height in the standing or sitting position, or both. The guest height is then compared to the predetermined height ranges to see what height range the guest falls within. In some embodiments, the height measurement apparatus may also comprise colored lights corresponding to the height ranges to indicate the height of the guest. Also, the apparatus may comprise an audio device to announce the height or height range so that an operator doesn't have to watch the lights or display. These outputs may remain on for a given amount of time and then turn off until the next measurement is taken.

The measurement system may or may not include height indicator identifying marks, and those marks may or may not be directly associated with inch marks, allowing the guest to see his/her exact height. Often, guests question the accuracy of these direct height read-out marks. However, a height read-out device such as a height check stick may be available should a guest demand learning what the specific height measurement read-out is. The system of the present invention may also include a direct height read-out, as with a numeric display such as an LCD or LED read-out.

Advantages of the present invention include accuracy and consistency in measuring guest height, including guests in wheelchairs. The present invention provides a near instant height measurement with minimal amount of input required by the employee to operate. The present invention provides a one-time measurement usable throughout a park or resort, eliminating time in re-measuring at each ride location, or any inconsistencies that result from the process. Prevention of errors by employees or tampering by a guest to override a proper measurement are greatly diminished. Efficiency will be increased because a measurement needs to be taken only once rather than at each attraction, saving employee time and guest waiting and frustration.

The present invention eliminates many problems in the art, such as a guest being stopped and measured multiple times throughout the day, or waiting in line for a ride to find that he/she does not meet the height requirement. With manual height checks at each ride, it is possible to meet the height requirement at one attraction but not at the next, even when the requirement is the same. This may be caused by employees drawing different conclusions as to whether or not the height requirement is met. All this may create angry guests that take frustrations out on employees and a negative experience for both guests and employees.

The method and apparatus of the present invention may have alternative embodiments. The measuring device may have a movable height measuring arm that is read mechanically or electronically within the device, which then generates a height indicia, such as a color-coded wristband. Alternatively, the height may be measured ultrasonically without the use of a movable height measuring arm. Instead of an ultrasonic signal, other signals may be used, such as light or radio frequency, or any other electromagnetic radiation.

The height measurement device may measure compliance with height requirements for attractions throughout the resort. Alternatively, or in addition, a single measurement device may be provided at a specific attraction to measure the height for only that attraction.

Measuring devices may be installed at information booths or other stations near the park entrance or at other locations within the resort. The devices may even be located outside the resort. Guests without indicia, such as wristbands, presenting themselves to an attraction may be measured at the attraction. For guests attending more than one resort or park, the wristbands or other indicia may be used at all resorts or parks minimizing inconvenience to the guests and increasing park and guest efficiencies.

Prior art indicia of height include hand stamps which may be difficult to read, and may also wash or rub off during the day. Such indicia alone, if determined by devices and methods not within the scope of the present invention, will not solve the problems of accuracy, consistency and efficiency addressed by the present invention.

BRIEF DESCRIPTION OF THE DRAWINGS

FIGS. 2a and 2b are schematics of one embodiment of the height measurement apparatus of the present invention.

FIGS. 4–12 are exemplary embodiments of the appearance of the height apparatus of the present invention.

DETAILED DESCRIPTION OF THE PREFERRED EMBODIMENTS

Figure 1A:
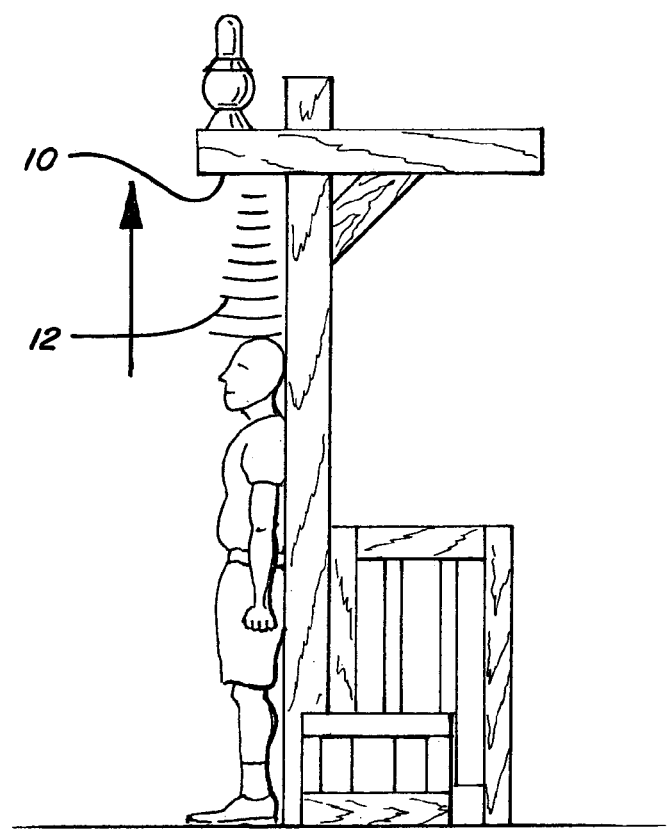
FIGS. 1a and 1b are schematics of one embodiment of the height measurement apparatus of the present invention.
Figure 1B:
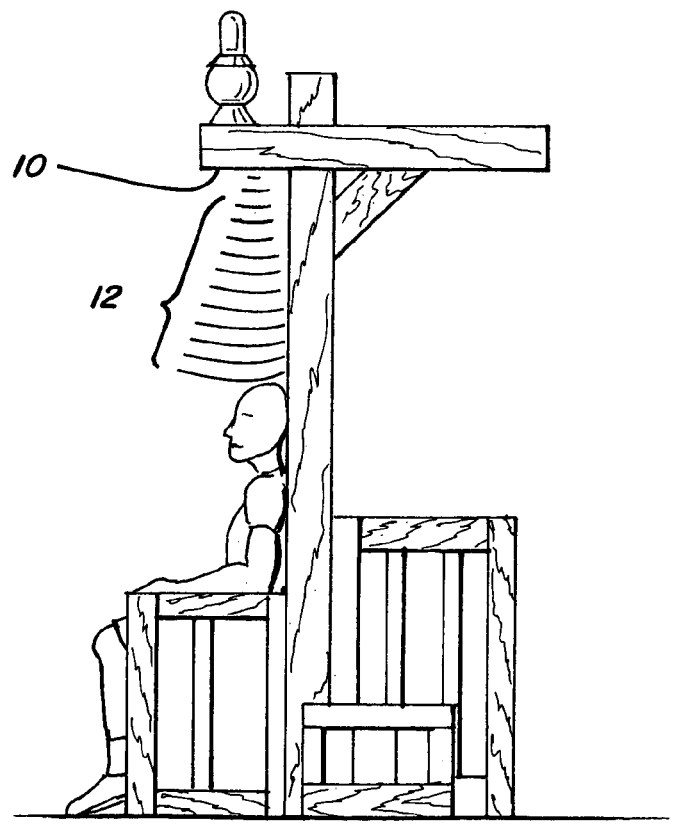
Figure 4:
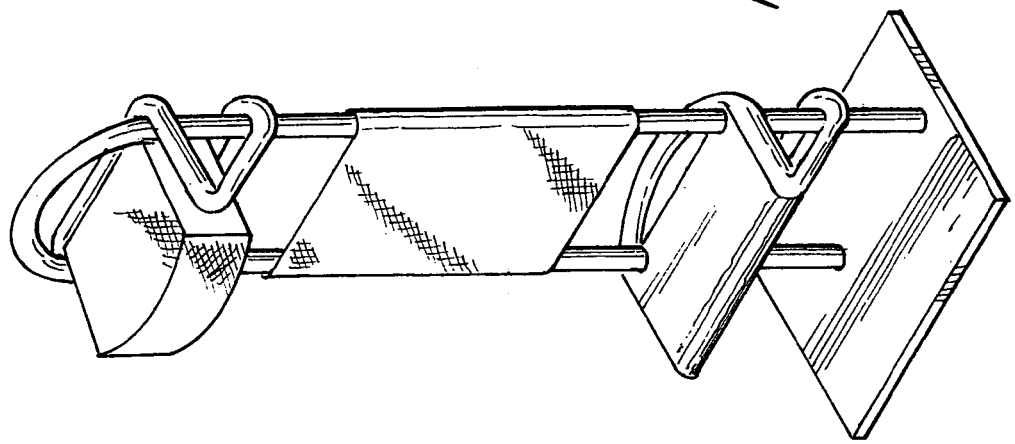

FIGS. 1a and 1b illustrate a height measurement apparatus in accordance with the present invention. FIGS. 1a and 1b depict structural components of one design of a height measurement system made to appear as part of a mining operation scene. Ultrasonic transducer 10 is mounted in a stationary position above a person's head. FIG. 1a shows the person in a standing position underneath sensor 10. FIG. 1b shows the person in a sitting position underneath sensor 10. The apparatus may additionally feature a back support to properly locate the person underneath the sensor and ensure that the person is in proper alignment with the sensor 10. The transducer 10 sends an ultrasonic pulse 12 towards the head of the person. The pulse 12 is reflected when it reaches the top of the person's head, and returns to the sensor. The amount of time for this travel is measured, and can then be translated into distance, as is well known in the art. The pulse emitter and sensor need not be directly overhead, but may be positioned in other convenient locations, such as overhead but at an outward angle.

In a preferred embodiment of the present invention, a paddle is placed to rest on top of the person's head in order to more accurately reflect the ultrasonic signal. Another exemplary embodiment of the height measurement apparatus of the present invention is illustrated in FIGS. 2a and 2b. The paddle 20 may preferably have a level indicator to help the operator keep the paddle level. A tilted paddle can lead to an inaccurate measurement. The paddle may also preferably have a button in the handle to allow the operator to signal taking a height measurement. In the embodiment shown in FIGS. 2a and 2b, the height measurement apparatus further utilizes a platform 24 on top of which the person stands in order to be measured. The platform provides a level surface to facilitate an accurate measurement. The height measurement apparatus shown in FIGS. 2a and 2b further comprises a roof or overhang 25 for housing the transducer, and also providing some shelter from the sun or rain.

The results of the height measurement may be reported in many different ways. In certain embodiments of the present invention, the height result may be reported with lights. The height measurement apparatus may have several lights of different colors which correlate to the different height ranges, as shown at 26 in FIGS. 2a and 2b. The resultant height range is reported by illuminating the corresponding colored light. The height apparatus can additionally report the result using sound or a numeric display.

Figure 3:
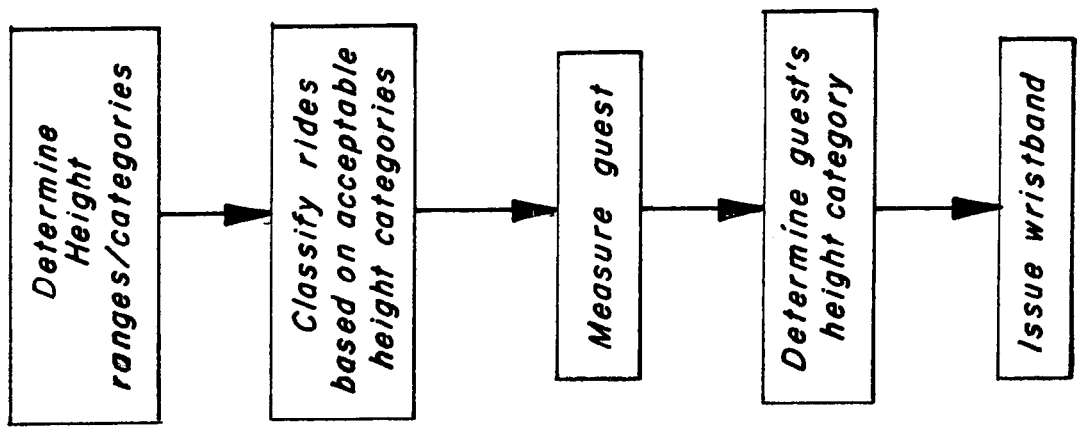
FIG. 3 is a flow diagram of the method of the present invention.
Figure 9:
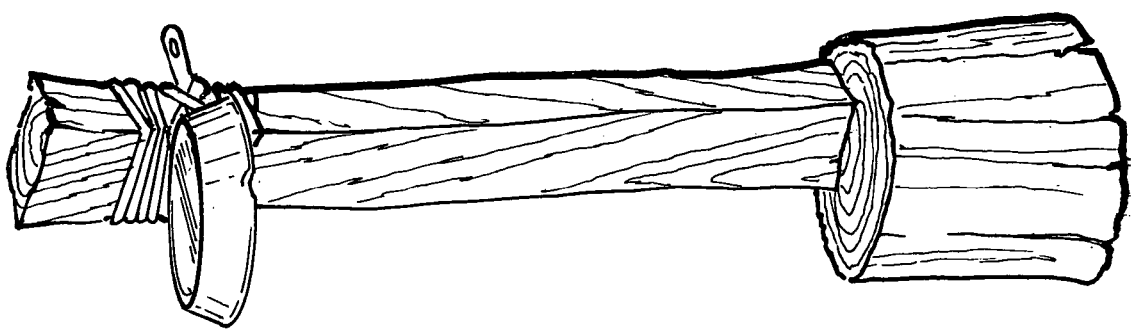
Figure 6:
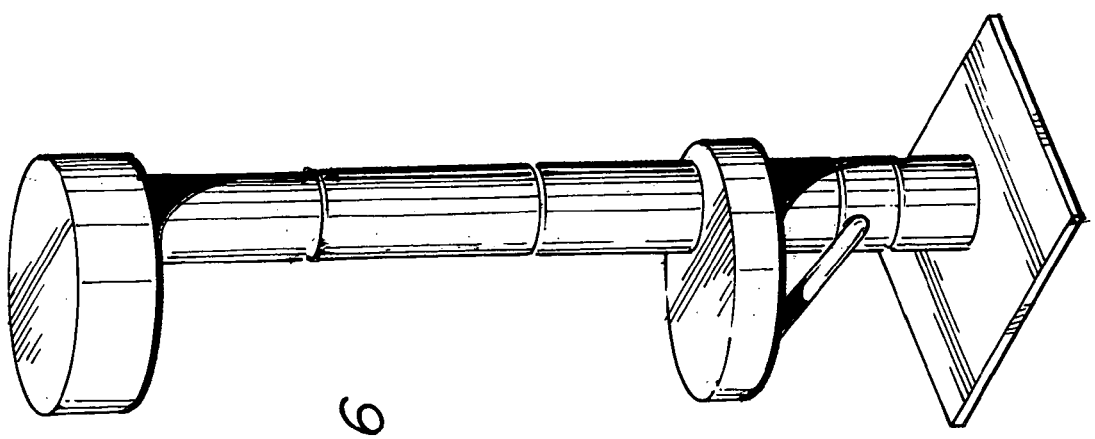
Figure 7C:
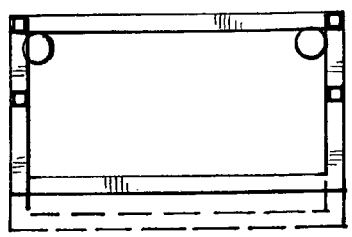
Figure 7A:
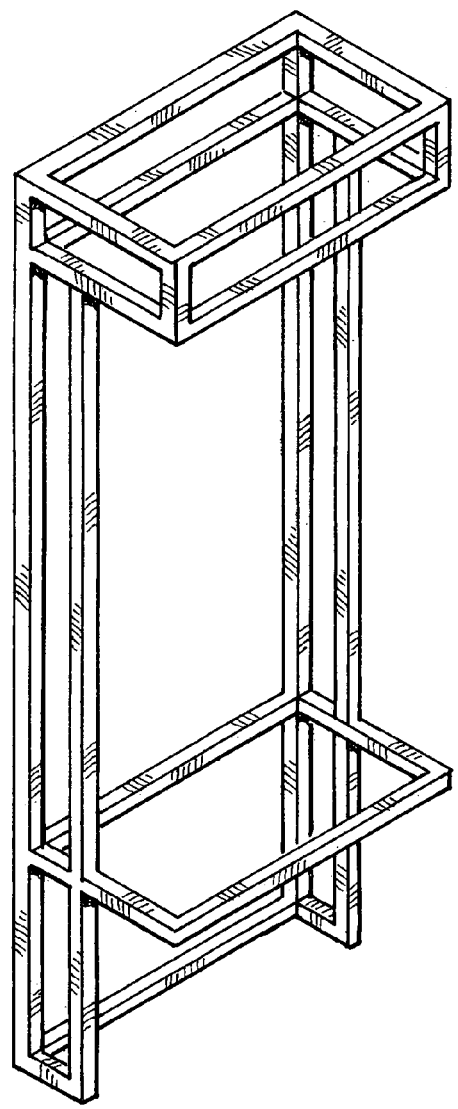
Figure 7B:
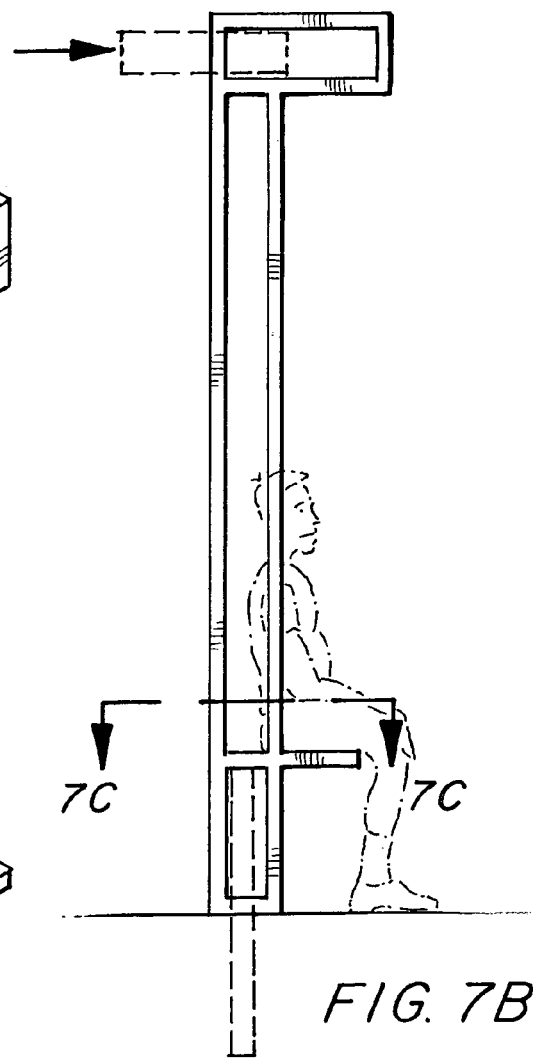
Figure 8:
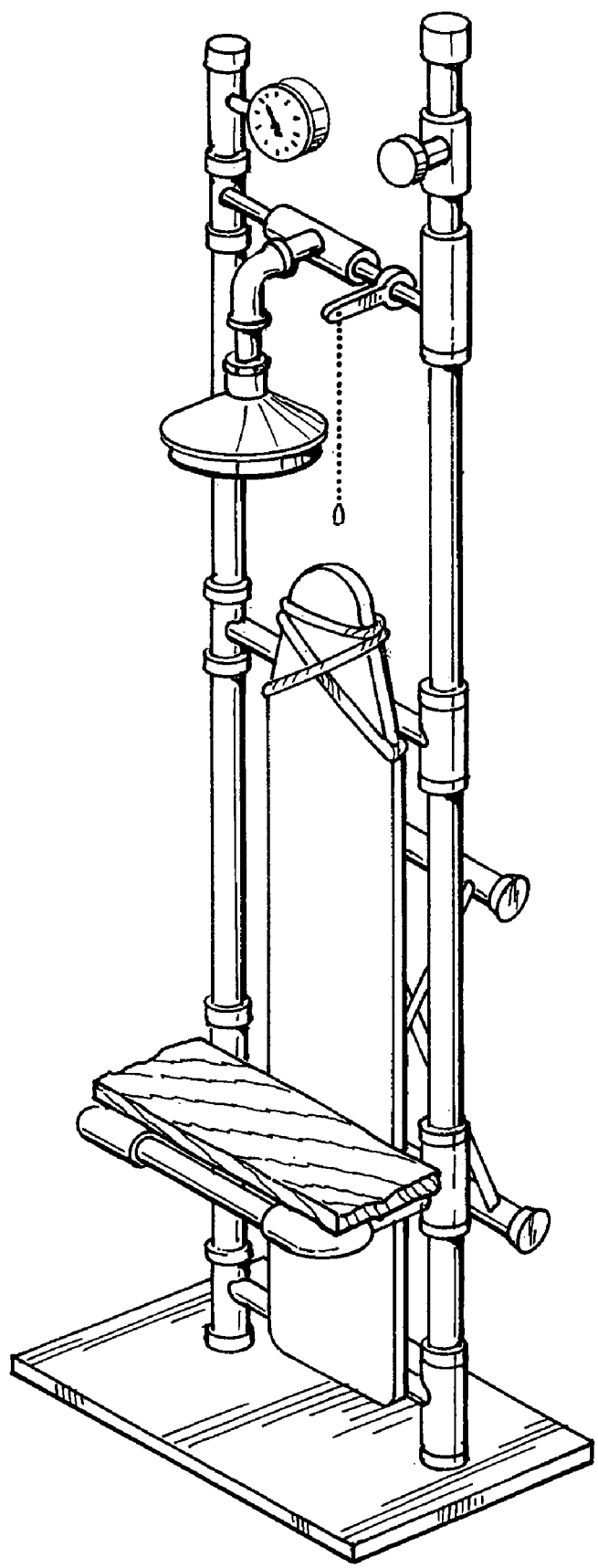
Figure 10:
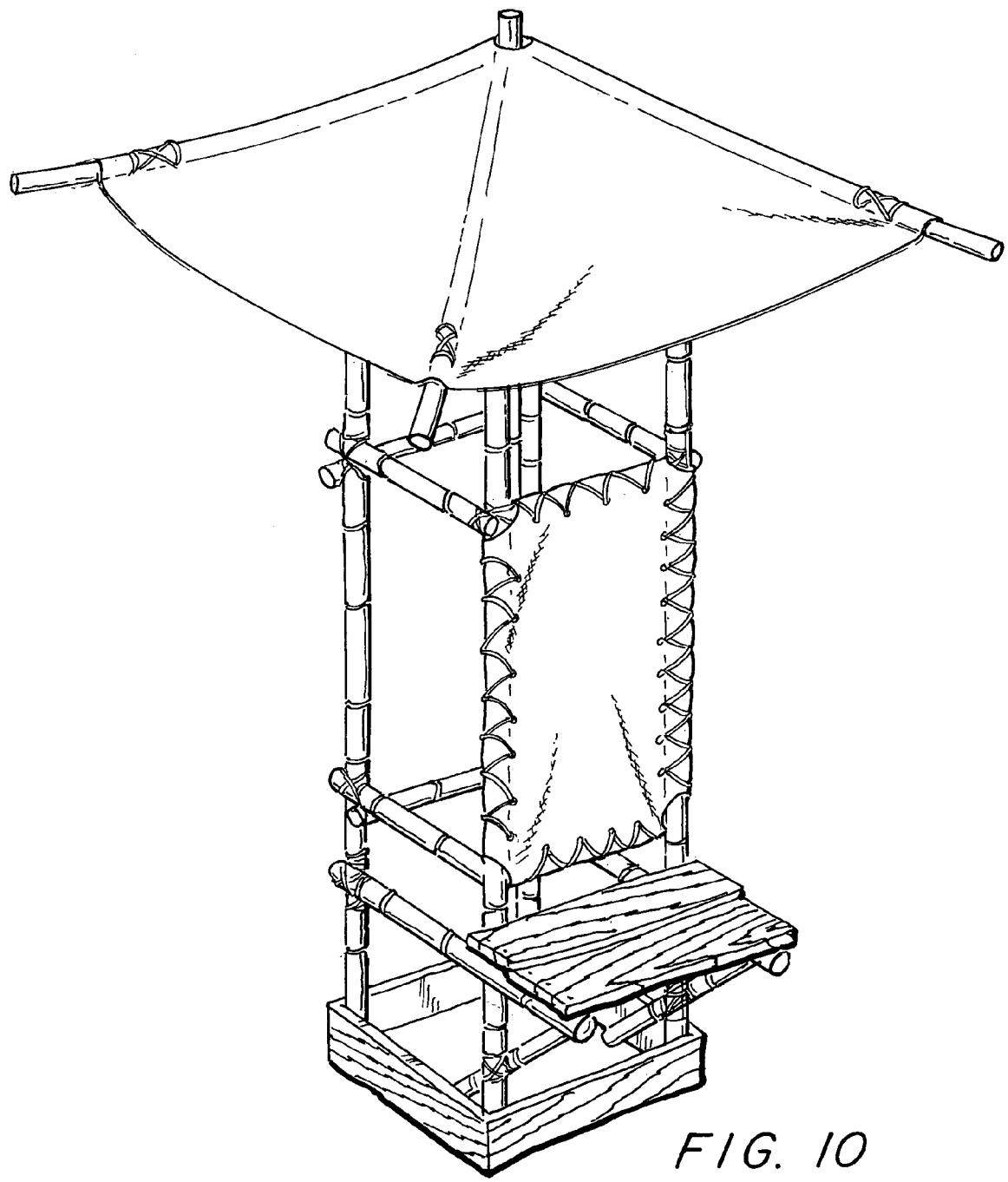
Figure 11C:
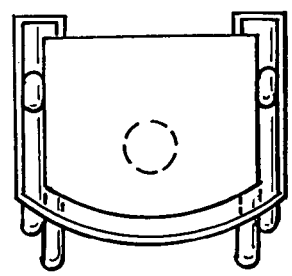
Figure 11A:
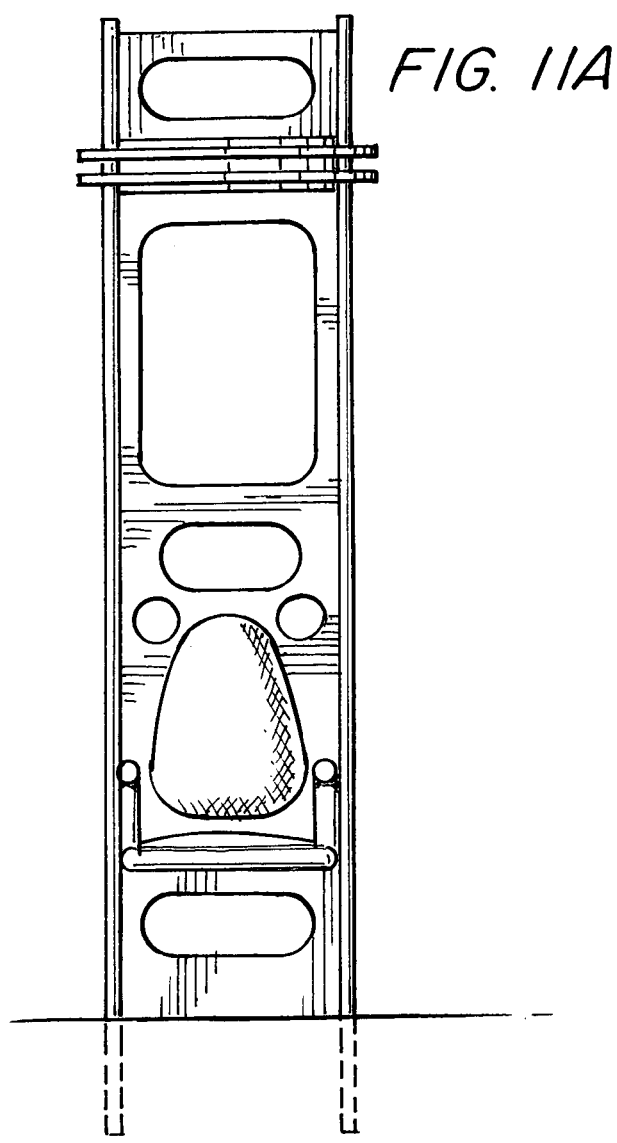
Figure 11B:
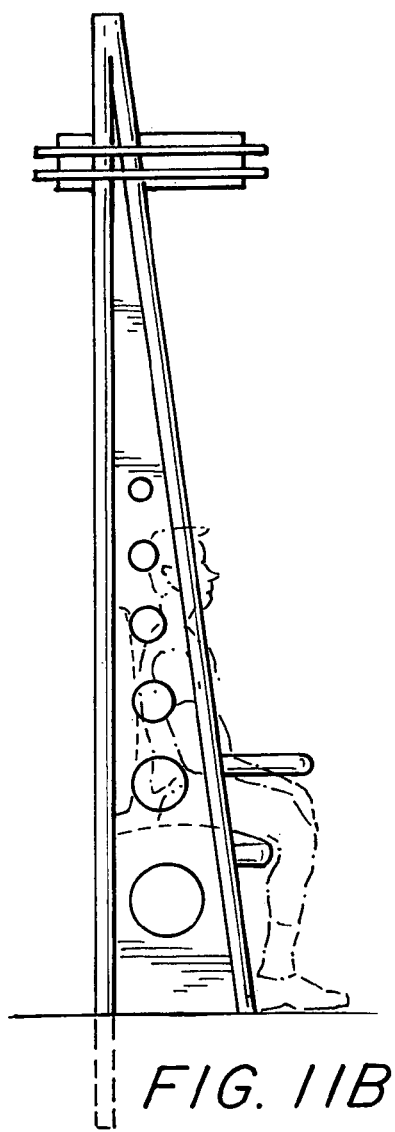
Figure 12A:
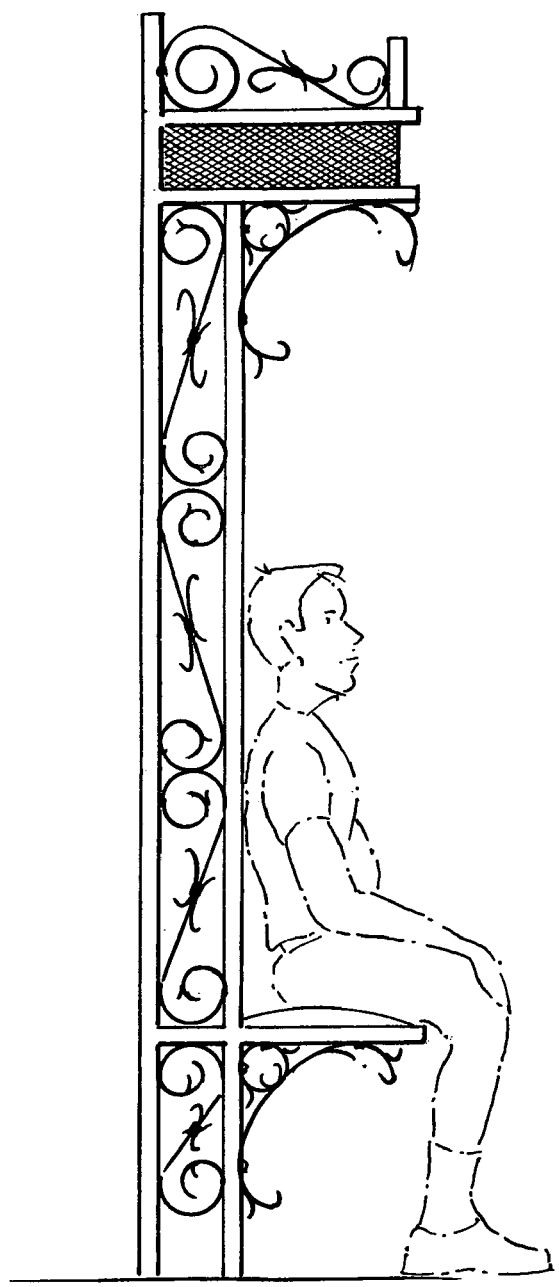
Figure 12B:
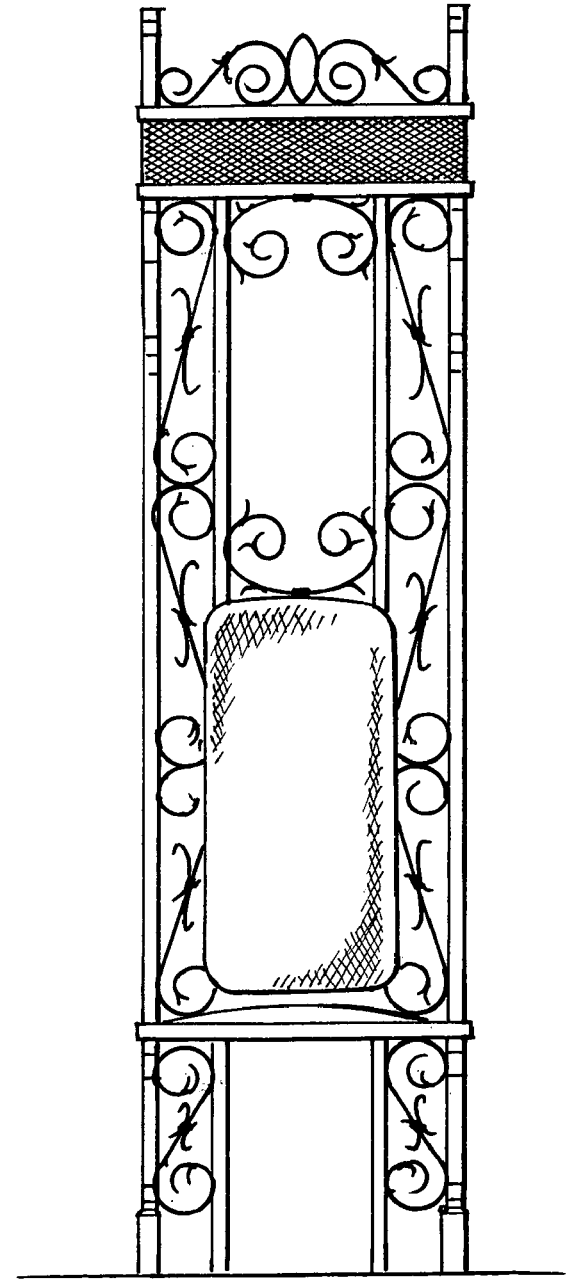

FIG. 3 is a flow chart which illustrates the general method of managing entrance to rides or attractions according to height requirements, as taught by the present invention. The method of the present invention provides a coding system including indicia associated with the height of a guest as measured by the apparatus of the present invention. In order to do this, a plurality of height ranges must first be determined. The height ranges should collectively span the heights of most visitors.

Once the height ranges have been determined, coding is assigned to each height range to more easily identify that height range. In the current embodiment of the invention, a different color is assigned to each height range. Other forms of coding are also envisioned. For example, visual symbols or designs, well known characters or figures, or names, may be assigned to each height range.

In the preferred embodiment, the attractions are individually color-coded corresponding to the height limitations at each attraction. Each attraction can be designated as accepting guests wearing certain colors of wristbands, which represent heights acceptable for entering the attraction. Notices may be posted throughout the park and/or in park guide maps and handouts indicating the requirements for each attraction by utilizing the indicia, such as the color-coding.

Next, guests must be measured. Each measured guest's height is compared to the different height categories to determine which category that guest falls within. Once the height range is determined, there must be a way to identify the person's height range. For example, a colored wristband may be affixed to the guest, each color representing a specific height or height range.

In order to ensure the height measurement apparatus takes accurate readings, the unit in the preferred embodiment should be zeroed before use. When the machine is first powered up, the operator will have to calibrate the machine to the ground, which is the reference plane for determining height. The calibration procedure then continues with the height check machine reading a known height to make sure it is working correctly and to allow the operator to adjust for problems that could lead to inaccuracies. When calibrating, an operator measures the height of a calibrated stick or rod. The stick is known height (for example, 35"), and the programmable logic controller makes adjustments based on how high it measures the stick. For example, suppose that when the machine measured the stick, the sensor reported that the stick was 35½" tall. The programmable logic controller would remember that the sensor was reading ½" too tall and subtract ½" from subsequent readings to compensate.

There are several problems that can be easily corrected by proper calibration of the apparatus. For example, a common problem is uneven ground. If the ground is not perfectly flat, the height check machine will either be on higher or lower ground than the person being measured. This will fool the machine into thinking that the person is shorter or taller (respectively) than they really are. Electronics can always become less precise over time, and give inaccurate readings. Maintenance procedures may also slightly change the height of the ultrasonic sensor. For reasons such as these, the unit is typically calibrated once at the start of each day, and re-calibrated each time it is moved.

In an exemplary embodiment, the paddle is placed at a pre-determined height, which could be, for example, approximately 35 inches from the ground. The height measurement button is pressed. If the position calibration is valid, a positive indicator will show, such as a yellow light illuminating. If the calibration is invalid (more than 1 inch off, for example), a negative indicator will show, such as no lights or a red light. The operator will need to turn power off then on and calibrate again. Once calibrated correctly, the machine will begin normal operation.

In a preferred embodiment of the present invention, the height measurement apparatus waits for a button to be pressed to initiate triggering the emitter and sensor. When the button is pressed the machine will activate the ultrasonic sensor. The apparatus then takes four samples during a short period, for example one second, and calculates the average of these readings. When the sample is valid, the height color will be illuminated, and the activation button can be released. Audio can also be enabled to announce the resultant height measurement. In this embodiment, the light will remain illuminated for four seconds after the button is released. After this sequence is finished, the machine will wait for the next button press.

Standard off the shelf industrial ultrasonic distance measuring sensors are used. An example of manufacturer is Banner Engineering, which produces the Q45U line of piezoelectric ultrasonic sensors. The ultrasonic sensors are preferably waterproof, so that they are not damaged in the rain. The sensors also preferably employ temperature compensation for variances in weather conditions.

The operator interface may be a simple interface such as an Allen Bradley MicroView terminal. The operator interface may offer a simple menuing system. From the main menu, the operator may view a history, or a "counts" screen where the number of counts for each height range is displayed. The operator has the option to reset this number. The operator interface may include other functions such as viewing the battery status.

FIGS. 4–12 depict several designs of the external appearance of the height measurement device of the present invention. These examples of external designs demonstrate that the apparatus may be made to look aesthetically pleasing without interfering with its function, and that the apparatus may determine height of a standing or seated guest. The figures depict alternative embodiments of the invention for both standing and seated guests, and describe functional and design features of alternative options.

The options include colored lights representing heights or height ranges determined by a sonar system. Alternative embodiments are also shown which do not employ a sonar or electromagnetic signal detection system, but rather a mechanical system. A wristband dispenser 21 may be incorporated into the height measurement apparatus of the present invention.

Furthermore, as mentioned previously, sonar may be replaced by an electromagnetic signal, including light or radar.

While the specification describes particular embodiments of the present invention, those of ordinary skill can devise variations of the present invention without departing from the inventive concept.

We claim:

1. A method of managing entrance to rides and attractions at a theme park according to height requirements, the method comprising the steps of:
   designating a plurality of height ranges;
   associating one or more rides or attractions within the theme park with one or more acceptable height ranges chosen out of said plurality of height ranges;
   measuring the height of a guest, wherein measuring comprises:
      abutting a substantially flat and level reflective surface to the top of a head of the guest, the surface not being worn by the guest;
      emitting a signal from a fixed point above the guest towards the guest and the reflective surface,
      detecting with a detector the signal reflected from the reflective surface;
      timing the return of the reflected signal; and
      calculating the height of the guest based on the time of return of the signal to the detector;
   associating the height of the guest with one or more of said plurality of height ranges;
   issuing indicia to the guest indicating the associated height range; and
   admitting the guest into a ride or attraction corresponding to the indicia issued to the guest.

2. The method of claim 1 wherein the signal is sonic.

3. The method of claim 1 wherein the signal is an electromagnetic wave.

4. The method of claim 1 wherein the signal is light in either the visible or invisible spectrum.

5. The method of claim 1 wherein the indicia is a wristband not removable from the wrist without breakage of the band.

6. The method of claim 1 wherein each height range is assigned a color and the indicia is correspondingly color coded.

7. The method of claim 1 wherein the height measurement is for a guest in a sitting position.

8. The method of claim 1 wherein the height measurement is for a guest in a standing position.

9. The method of claim 1 wherein the height measurement is taken upon entrance to the theme park.

10. An apparatus for measuring a person's height, the apparatus comprising:
   a signal generator mounted at an elevation higher than the person's head;
   a substantially flat and level reflective surface abutting the person's head wherein the reflective surface is not worn by the person;
   said signal generator emitting a pulse which contacts the reflective surface and is thereby reflected;
   a sensor which receives the reflected pulse;
   a programmable calculator coupled to the sensor; and
   programming in the calculator to determine the height of the person based upon the time of return of the reflected pulse.

11. The apparatus of claim 10 wherein the sensor is integral to the signal generator.

12. The apparatus of claim 10 wherein the signal is sonic.

13. The apparatus of claim 10 wherein the signal is an electromagnetic wave.

14. The apparatus of claim 10 wherein the signal is light of any frequency within the visible and invisible spectrum.

15. The apparatus of claim 10 further comprising lights to display the results.

16. The apparatus of claim 10 further comprising a speaker for playing sound to report the results.

17. The apparatus of claim 10 wherein the person is in a standing position.

18. The apparatus of claim 10 wherein the person is in a sitting position.

* * * * *